United States Patent [19]

Schnur et al.

[11] Patent Number: 5,079,600
[45] Date of Patent: Jan. 7, 1992

[54] HIGH RESOLUTION PATTERNING ON SOLID SUBSTRATES

[76] Inventors: Joel M. Schnur, 6009 Lincolnwood Ct., Burke, Va. 22015; Paul E. Schoen, 5006 Taney Ave., Alexandria, Va. 22304; Martin C. Peckerar, 12917 Buccaneer Rd., Silver Spring, Md. 20904; Christie R. K. Marrian, 6805 Kenyon Dr., Alexandria, Va. 22307; Jeffrey M. Calvert, 6033 Wilmington Dr., Burke, Va. 22015; Jacque H. Georger, Jr., 8409 Great Lake Rd., Springfield, Va. 22153

[21] Appl. No.: 182,123

[22] Filed: Apr. 14, 1988

Related U.S. Application Data

[63] Continuation-in-part of Ser. No. 022,439, Mar. 6, 1987.

[51] Int. Cl.$^5$ .................. H01L 27/12; B05D 5/12
[52] U.S. Cl. ........................ 357/4; 357/23.7; 427/54.1; 427/98
[58] Field of Search .......... 428/546; 427/96-98, 427/54.1; 357/4, 23.7

[56] References Cited

U.S. PATENT DOCUMENTS

| 3,884,704 | 5/1975 | Bantell | 427/98 |
| 4,199,649 | 4/1980 | Yundt | 427/96 |
| 4,539,061 | 9/1985 | Sagiv | 427/407.1 |
| 4,587,203 | 5/1986 | Brault | 427/54.1 |
| 4,661,372 | 4/1987 | Mance | 427/54.1 |

FOREIGN PATENT DOCUMENTS

2144653 A  3/1985  United Kingdom ........... 427/58

OTHER PUBLICATIONS

B. H. Tredgold and G. W. Smith, "Formed by Adsorption and by the Langmuir-Blodgett Technique", I.E.E. Proc., vol. 129, PTI., No. 4, Aug. 1984, pp. 137-140.

Primary Examiner—Peter A. Nelson
Attorney, Agent, or Firm—Wolf, Greenfield & Sacks

[57] ABSTRACT

A process for producing metal plated paths on a solid substrate of the kind which has polar functional groups at its surface, utilizing a self-assembling film that is chemically absorbed on the substrate's surface. The solid substrate may, for example, be an insulator of the kind used for substrates in printed circuitry or may, as another example, be a semiconductor of the kind used in semiconductor microcircuitry. The chemical reactivity in regions of the ultra-thin film is altered to produce a desired pattern in the film. A catalytic precursor which adheres only to those regions of the film having enough reactivity to bind the catalyst is applied to the film's surface. The catalyst coated structure is then immersed in an electroless plating bath where metal plates onto the regions activated by the catalyst.

34 Claims, 2 Drawing Sheets

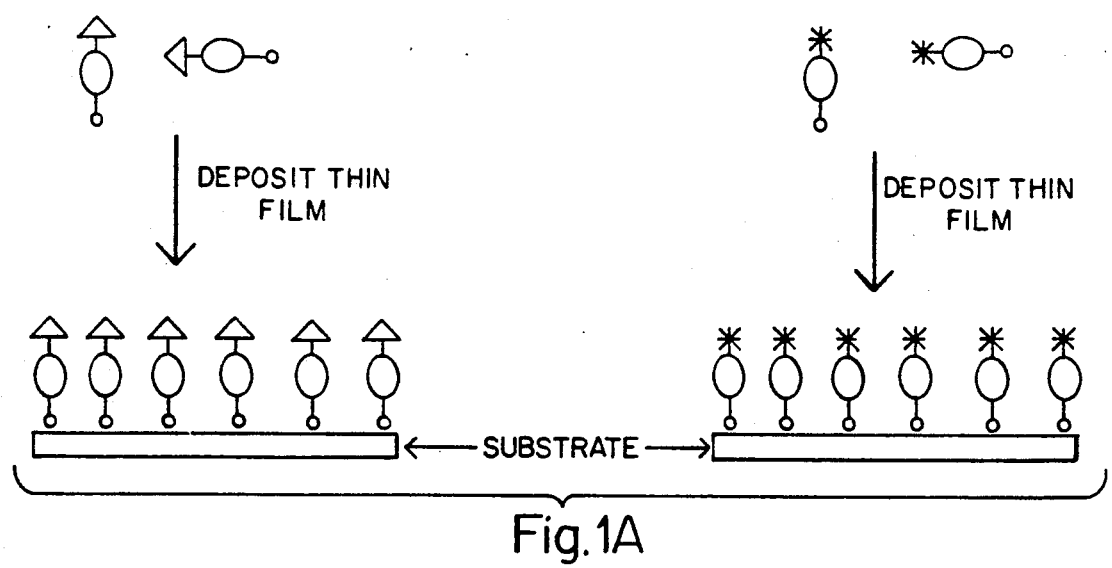
Fig. 1A
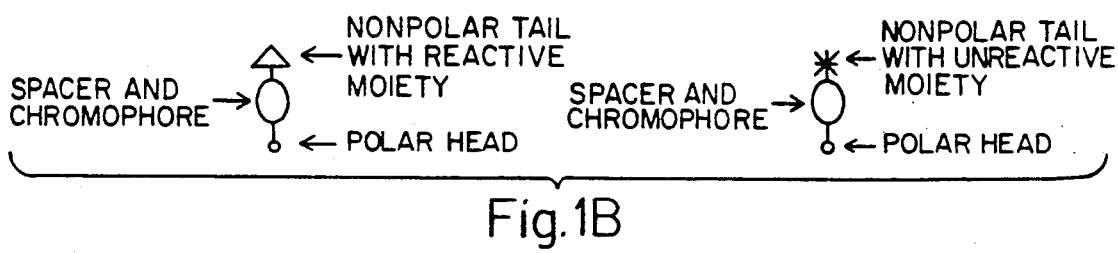
Fig. 1B
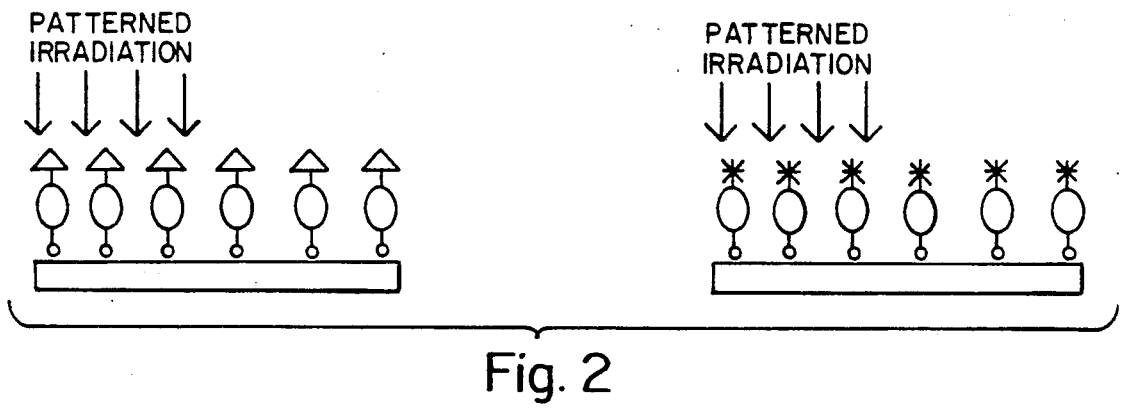
Fig. 2
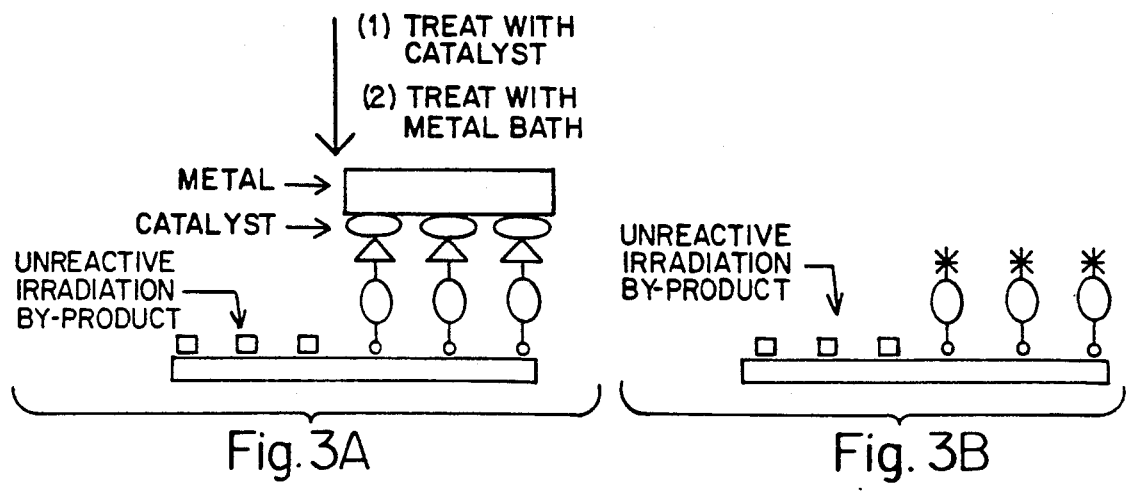
Fig. 3A
Fig. 3B

HIGH RESOLUTION PATTERNING ON SOLID SUBSTRATES

U.S. GOVERNMENT RIGHTS IN THE INVENTION

This invention was made jointly by four employees of the Naval Research Laboratory, Washington, D C. and two employees of Geo-Centers, Inc. The two Geo-Centers employees, at the time the invention was made, were in the performance of work under Naval Research Laboratory contract N00014-85-C-2243. The United States of America has certain rights in the invention arising out of that contract, including a nonexclusive, nontransferable, irrevocable, paid-up license to practice the invention or have it practiced for or on behalf of the United States throughout the world. The United States of America may also have rights in the invention derived from the four employees of the Naval Research Laboratory who are joint inventors of this invention.

RELATED APPLICATION

This application is a continuation-in-part of U.S. Pat. Application Ser. No. 07/022,439 filed Mar. 6, 1987.

FIELD OF THE INVENTION

This invention relates in general to the production of patterned films on solid substrates with use of a patterned irradiation step. More particularly, in one embodiment the invention pertains to ultra-thin films that provide desired surface characteristics on substrates to which the films are strongly adherent Yet even more particularly, the invention concerns procedures whereby areas of widely varying reactivity can be created with sub-micron lateral resolution on the substrate's surface. The invention enables the deposition of patterned thin metal coatings on semiconductor, dielectric or conductive surfaces as a direct consequence of the differential reactivity.

The ability to spatially tailor surface chemical properties has significant technological applications, especially in the field of microelectronics. The invention is particularly useful for the fabrication of high-resolution resists, masks, and conductive paths that are essential to the production of integrated semiconductor devices. The invention is also useful for the production of high-resolution conductive paths on insulating substrates such as quartz, alumina, and organic polymers for printed circuits and microwave circuits.

Although the deposition of metal on substrates in selected areas (commonly referred to as "selective patterning" or "selective deposition") relates to the making of both printed circuits and integrated circuits, the resolution requirements are sufficiently different that the two technologies will be treated separately herein.

BACKGROUND OF THE INVENTION

A. In Relation to Semiconductor Microlithography

Ongoing efforts to produce electronic devices of higher speed at lower cost has led to the search for more efficient methods of fabricating high-resolution, high-density integrated circuitry on semiconducting substrates such as doped silicon and gallium arsenide. One aspect of that search is the investigation of methods for producing patterns of high resolution, i.e., patterns having line widths of less that one micron (a micron is one millionth of a meter), an area of research known as microcircuit lithography. For a detailed description of this subject, see the book entitled "Introduction to Microlithography", L.F. Thompson, C.G. Willson, and J.J. Bowden, editors, ACS Press, NY (1983). At the present rate of miniaturization of integrated circuitry, it is anticipated that a resolution of approximately one quarter of a micron (i.e. $0.25\mu$) will be required within the next decade. For a discussion of the current state of the art in microlithography and an assessment of future requirements, see the monographs entitled, "The Submicron Lithography Labyrinth", A.N. Broers, Solid State Technology, June 1985, pp. 119 to 126; and "Materials for Integrated Circuit Process Technology", M.C. Peckerar, Academic Press, 1988.

In conventional fabrication of integrated circuits, patterning of the semiconductor surface is accomplished using the following general procedure. A radiation-sensitive organic coating (a "photoresist") is applied to the wafer surface. Prior treatment of the wafer with an adhesion-promoter such as hexamethyldisilazane is often employed. The coated surface is exposed to patterned radiation such as light, electron beams, ion beams or X-rays. Exposure is made either by the "flood" or by the "scanning beam" technique. In flood irradiation, all the regions to be irradiated are exposed simultaneously. Patterned radiation is achieved either by projecting an image onto the substrate or by interposing a mask between the light source and the substrate. In the beam technique, the work is broken into small regions, or "pixels" that are exposed sequentially, generally by causing the beam to trace out the desired pattern. A "positive" resist material is one in which the irradiated region becomes more soluble, for example, by photo-induced bond scission. A "negative" resist material is one in which the irradiated region becomes less soluble, generally due to a cross linking reaction such as condensation or free-radical polymerization. Chemical development (e.g., exposure to concentrated sodium hydroxide or chlorinated hydrocarbon solvent) leaves behind a pattern of insoluble organic material. Exposure to an ion plasma or etchant solution removes substrate material in the uncovered areas. Residual organic material is chemically stripped, revealing the etched "troughs" and the unetched "plateau" regions that were protected by the resist Some of the prime considerations in the commercial production of integrated microelectronic circuitry are: resolution of the features in the semiconductor substrate; throughput; uniformity and reproducibility; and capital equipment and materials cost. Electron beam irradiation of multilayer films of vinyl stearate and omega-tricosenoic acid, deposited using the Langmuir-Blodgett technique, has produced 60 nm wide lines and spaces (see: A. Barraud, et. Al., Thin Solid Films, 68, 1980, pp 91-100; also, A. Broers and M. Pomerantz, Thin Solid Films, 99, 1983, pp. 323-329).

A number of drawbacks exist with beam lithographic techniques. First, computer-controlled beam systems require considerable capital expenditure and are expensive to maintain. Second, the sequential irradiation of individual pixels is far more time-consuming than flood irradiation techniques due to limitations in the exposure sensitivity of the resist material. Throughput considerations (i.e., the time required to produce the item) take on greater significance as feature density and wafer size both continue to increase Third, there is a tradeoff between resolution in the resist and etch resistance It is known that the energy lost by electrons beamed into a solid is scattered in an oblong pear-shaped volume of diameter roughly equal to the electron penetration depth. The penetration depth increases with the energy of the incident electrons Consequently, the diameter of the exposed area is at a minimum when the penetration depth is equal to the film thickness (positing the requirement that the entire thickness of the film be irradiated). Therefore, a means of obtaining improved resolution is by use of a thinner resist film, such as spin-cast organic polymer films or the Langmuir-Blodgett films described previously. However, ultra-thin organic film resists suffer from a number of problems that include film inhomogeneity (particularly pinholes) and the inability to withstand the vigorous plasma etching processes used to transfer the features of the resist to the underlying substrate.

Optical lithographic processes are the most widely employed because they offer the best combination of resolution and throughput. At the present time, the limit of resolution of microcircuitry features that can be produced on a scale practical for commercial production is on the order of one micron. Optical lithography generally involves patterned UV (400 nm or below) irradiation of semiconductor substrates coated with a spin cast organic resist film that is usually 300 nm to one micron thick. Principal limitations to attainment of higher resolution are due to a combination of the wavelength of light employed, the film composition, and photoresist thickness.

In optical lithography, it is known that resolution varies inversely with the wavelength of the irradiation. Therefore, high resolution is achieved by using radiation of the shortest possible wavelength to which the resist is sensitive. A number of light sources suitable for UV irradiation are available, including mercury lamps, xenon lamps, deuterium lamps, surface plasma discharge sources, Nd-YAG lasers, excimer lasers, and optical harmonics generated from the sources. Most of the currently-used high resolution photoresists are sensitive to near-UV (i.e., 320 to 400 nm) light Few, if any known photoresists are useful in the deep-UV (200 to 320 nm) or the vacuum-UV (below 200 nm) regions.

The wavelength of ultraviolet radiation is in the 4 to 400 nm range. That range is loosely divided into near-UV (400 to 300 nm), far-UV (300 to 200 nm), and deep-UV (below 200 nm). Deep-UV radiation is strongly absorbed by air and therefore is usually used in an evacuated apparatus. For that reason, deep-UV is often refered to as "vacuum-UV"

As discussed above for beam techniques, the spin-coated resist films used in optical lithography must be at least several tenths of a micron thick to avoid pinholes and provide adequate resistance to plasma etching. Other limitations to resolution with the use of thick films arise from defocussing of the image in the film, the occurrence of standing waves in the film, Rayleigh scattering from film inhomogeneities and from reduced control of the spatial extent of photoreactions. Spin coating tends to produce films that are thicker at the edges than in the center. Variations in the thickness of the film causes loss of resolution during contact mask exposure (i.e., where a patterned mask is in direct contact with the resist-coated substrate) due to diffraction and defocusing problems. Additionally, spin-coating machines are expensive and the substrates must be coated serially (i.e., one after the other).

Once patterned, conventional optical photoresists generally require chemical development of the image (i.e., removal of the soluble resist material). Solvents employed in development, especially chlorinated hydrocarbons, are known to be particularly environmentally hazardous. Resolution (especially edge acuity) degradation is also induced during development by imperfect dissolution of the resist Other difficulties encountered with known resist films include imperfect or weak adhesion to the substrate, which can render the piece of work useless if needed resist regions come loose from the substrate. Resist materials often require special care in handling due to their sensitivity to ambient light, moisture and temperature.

Fabrication of metal paths on a semiconductor substrate can be accomplished in a number of ways Generally, a thin metal coating is applied by vapor or sputter deposition over the entire area of the substrate. Most of the metal is removed in a later step following patterning and development steps. No commercial optical lithographic process are believed to currently exist whereby high resolution metal patterns can be selectively deposited.

B. In Relation To Printed Circuitry

In the fabrication of printed circuits, adherent metal patterns are produced on insulative substrates such as organic polymers (e.g., acrylonitrile-butadiene-styrene or polysulfone) and metal oxides (e.g., aluminum oxide). As in the case of semiconductor substrates, metal patterns are generally formed by vapor deposition followed by patterning and removal of most of the metal layer although many other methods are often used.

A variety of procedures are known for the selective deposition of metal initially in only the desired areas of the substrate. In one such procedure employed with a polymeric substrate, a patterned photoresist layer is etched by an acid and the etched resist surface is then activated for metal deposition by exposure to a solution of tin salts and noble metal salts which are applied consecutively or are applied jointly as a mixture. After activation of the etched surface, the substrate is immersed in an electroless plating bath. A typical electroless plating bath contains metal ions, complexing agents, stabilizers and a reducing agent. The reducing agent causes the complexed metal ions to be reduced to metal only in the activated regions. The plated metal surface is itself catalytic for further metal deposition, thus the thickness of the plated layer can be varied by regulating the length of time in which the substrate is immersed in the plating bath. For a report on the technical literature (including patents) pertaining to electroless plating of metal onto polymer substrates, see the monograph entitled "Plating of Plastics -- Recent Developments" by F.A. Domino, Chemical Technology Review No. 138, Noyes Data Corporation, New Jersey (1979).

The general method described above has been employed to produce patterns with 150 micron resolution on epoxy substrates (J K Dorey, et. al., U.S. Pat. No. 4,537,799; granted Aug. 27, 1985). In a related report, metal lines 100 microns in width were fabricated on a polyphenylene sulfide substrate using a procedure in which laser annealing and chemical doping replaced the development and etching steps. These methods involve a considerable number of steps, making them time-consuming and expensive, especially in comparison to the present invention.

It is known that selective activation of an insulative substrate can be accomplished by using stamps or stencils to deposit an "ink" containing either reducible metal complexes or redox reagents that reduce activating metal ions on the substrate surface to produce a metal plate. The resolution of the metal pattern produced by this method is severely limited by the physical size to which the stamp or stencil can be reduced. This general procedure is employed to produce metal patterns on ceramic substrates. It is known that a reducible metal complex, applied as a mixture with a polymeric binder through a stencil to an alumina substrate, can be transformed to a metal pattern by heat treatment. The drawbacks of this method include limited feature resolution, problems with adherence of the metal to the substrate and an expensive firing process.

OBJECTS OF THE INVENTION

A. In Relation To Semiconductor Microcircuitry

An object of the invention with respect to the technology of semiconductor microcircuitry is to provide a photsensitive film which may be patterned at high resolution by irradiation with an electron beam or by irradiation with light whose wavelength is preferably less than the 320 or 400 nm wavelength of the conventionally employed near-UV light, that does not require chemical development, that has significantly less pinholes, that is strongly adherent to the semiconductor substrate, that is more tolerant of varying environmental conditions than conventional resists, that can cause chemical reactions (such as metal depositions) to occur selectively in the exposed or unexposed regions and that retains its integrity under conditions of long exposure (i.e. many minutes) to the reactive ion plasmas now used in fabricating semiconductor microcircuits. In short, the principal objective of the invention is to provide an ultra-thin high resolution resist that does not have the drawbacks associated with the high resolution resists heretofore used in the fabrication of semiconductor microcircuits.

Another object of the invention is to provide a method of making microcircuits using conventional electroless plating technology to produce high resolution patterns on semiconductor substrates.

A further object of the invention is to provide an ultra-thin high resolution, strongly adherent, etch-impervious, resist pattern on a substrate which can be conductive, semiconductive or dielectric.

Yet another object of the invention is to provide a method of making high-resolution metal patterns using standard wet chemistry techniques that avoid the need for complicated or expensive equipment such as the vacuum systems employed in some of the microcircuit fabricating methods now in use.

Another object of the invention is to produce an ultra-thin high resolution resist that remains stable over a wide temperature range and is sufficiently tolerant of high humidity so that specialized atmospheric control equipment is not needed for the protection of the resist.

Still another object is to form visible and u.v. opaque high resolution metal patterns on optical and u.v. transparent substrates for the purpose of fabricating, replicating and repairing lithographic masks.

B. In Relation To Printed Circuitry

The principal object of the invention with respect to the technology of printed circuitry is to provide a quick, simple, and inexpensive method of producing high-resolution conductive pathways on an insulative substrate.

Another object of the invention with respect to the technology of printed circuitry is to provide a method whereby adherent metal patterns can be produced on an insulative substrate.

A further object of the invention with respect to the technology of printed circuitry is to provide a method for the selective deposition of metal on an insulative substrate.

Another object of the invention with respect to the technology of printed circuitry is to provide a method of producing printed circuits utilizing relatively non-hazardous aqueous electroless plating solutions that are commercially available in bulk and are relatively inexpensive.

THE DRAWINGS

FIG. 1A schematically depicts the formation of a monomolecular film on a solid substrate by chemisorption of molecules from a homogeneous solution onto the surface of the solid substrate.

FIG. 1B diagramatically defines the symbols used in the drawings.

FIG. 2 schematically depicts the patterned irradiation of the monolayer film to cause a change in the reactivity of predetermined regions of the monolayer.

FIG. 3A schematically depicts the adherence of the colloidal catalytic precursor to the remaining reactive moieties at the silane molecules and the formation of a metal plate on the monolayer film.

FIG. 3B schematically depicts the unreactive silane monolayer and unreactive byproduct of irradiation.

FIG. 4A schematically depicts the profile of a semiconductor substrate after an ion etch and shows the metal film on the plateau formed by etching of the substrate.

FIG. 4B schematically depicts the formation of a monomolecular film on the irradiation byproduct by chemisorption of colloidophilic molecules from a homogeneous solution.

FIG. 5A schematically depicts the stripping of the metal/colloid catalyst after etching.

FIG. 5B schematically depicts the adherence of the colloidal catalyst precursor to the colloidophilic molecules and the formation of a metal plate on the monolayer film.

SUMMARY OF THE INVENTION

According to the invention, a process of producing patterned molecular assemblies on a substrate is carried out by providing a substrate having at least one layer of radiation reactive material having substantially equal reactivity over a surface. The surface of the radiation reactive material is exposed to patterned radiation to create spatially spaced first and second areas of different reactivity. At least one additional layer of material is built directly on one of said first and second areas to create a patterned substrate.

The invention can comprise a process for producing metal patterns on a substrate by causing a layer or film on the surface of the substrate to be altered in its reactivity. Preferably a catalytic precursor is adhered only to those regions of the film that have sufficient reactivity to bind the catalytic precursor and then the substrate is placed in an electroless metal plating bath whereby a metal plate is produced in those regions having the catalytic precursor thereon. Preferably, the substrate is of the kind having a polar-functional group at its surface and the monomolecular film is a self-assembling film which is deposited on the surface of the substrate and can be a monomer or polymer.

It is a feature of this invention that high-resolution conductive paths which can be spaced apart distances of 0.1 microns or less can be made. The invention is particularly important in connection with semi-conductor microlithography, electrical device manufacture, printed circuit production, mask duplication, manufacture and repair.

Description of Preferred Embodiments

Figure 4A:
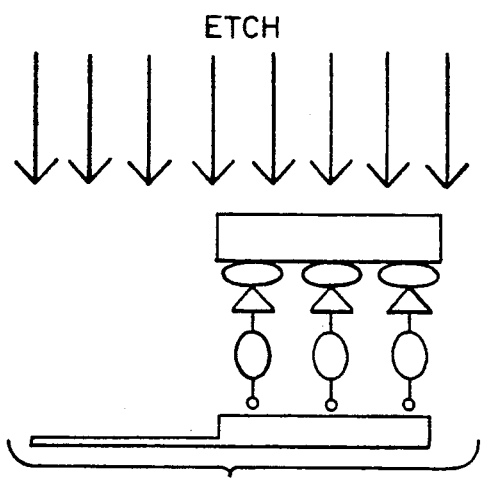
Figure 4B:
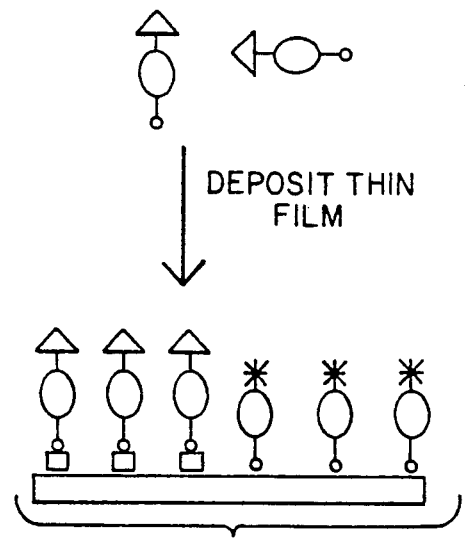

Several terms are used in this application which have meaning as described below. "Ultra thin film" refers to films or layers which are at least one molecule thick. Often, the films used are thinner than about one quarter of the wavelength of light used to expose the substrate, and may be as thin as a monomolecular layer.

"Radiation reactive material" as used herein is a material reactive to radiation that can absorb radiation used to expose it and which undergoes a modification as a result of absorption of the radiation. Preferably, the radiation reactive material will absorb light with a wavelength of less than 400 nanometers. Most preferably the radiation reactive material will have an absorption maximum at the wavelength used to expose the material. Radiation reactive materials include organic, inorganic and polymeric materials. Polymeric materials include polyethers, polyurethanes, polysulfones, polystyrene, polyamides, polymethacrylates, polybutadienes, polyethylene terphthalate, paraffin, polyisoprene and blends and copolymers of such materials. Inorganic materials include chlorosilanes, methoxysilanes, ethoxysilanes, silazanes, titanates, zirconates, and the like.

"Irradiation" can be any electromagnetic wave which causes a change in the reactivity of the surface to be treated. In conventional photolithography with thick (ca. 1 micron) photoresists, the overall resolution of the process is directly proportional to the wavelength of light which causes the change in the reactivity of the layer or film. Therefore, it is preferred to use irradiation which would be shorter than 500 nm in order to achieve a theoretical resolution of less than 0.5 microns and even more preferred to use irradiation shorter than 250 nm in order to achieve a theoretical resolution of less than 0.25 microns in the claimed process. Because this process can also utilize ultra-thin films that are considerably thinner than the wavelength of the patterning radiation, it is possible to use near-field optics to achieve potential feature resolution on the order of tens of nanometers. A discussion of near-field optics can be found in the manuscript by U. Durig, et al., IBM J. Res Develop., Vol. 30, pg. 478 (1986) entitled "Near-Field Optical Scanning Microscopy with Tunnel-Distance Regulation".

Resolution refers to the space between deposited lines such as metal lines or line width deposited Line thickness or height itself as in the metal deposit can be very small in the angstrom range or higher. Irradiation in patterns can be accomplished by any of the known conventional techniques such as direct write electron or laser beam, projection step and repeat, proximity printing, contact printing.

A "catalytic precursor" is a term commonly used in the field of electroless plating to wear a chemical compound or particle, such as a palladium-tin colloid, that can cause electroless metal deposition onto areas of a substrate to which the catalytic precursor has been attached.

A "patterned molecular assembly" is meant to refer to a structure built up on the surface of a substrate which conforms to a preselected pattern. The pattern is that pattern created by patterned irradiation. The molecular assembly can be a single layer of one material or multiple layers of the same or different materials. These materials include inorganic, organic materials, as for example semiconductive, metallic or combinations of these materials. For example, the first layer can be one type of metal such as palladium bound to the most reactive of the spatially different areas of reactivity and the second layer may be a different metal such as copper bound to the palladium Other layers may be further applied as may be needed for a particular application. Alternatively, irradiation reactive material such as a particular chlorosilane can be exposed and then a second chlorosilane can be built up selectively in the most reactive areas. If the first reactive material is UTF4 and UTF3 is the second reactive material, in this case the UTF4 will be bound to the unexposed areas and therefore, UTF3 will be bound only in the unexposed areas. Assemblies can be built up further by introducing a palladium-tin colloid which will bind to the most reactive of the spatially different areas of reactivity and a third layer may be built up such as nickel which can then have a fourth layer of copper built onto it. A molecular assembly in this case would be a sandwich structure of UTF3/Pd-Sn/Ni/Cu.

"Spatially different areas of reactivity" are composed of high resolution patterns of different chemical moieties created when a radiation reactive material at its surface layer, is exposed in a pattern with the proper irradiation wavelength The spatially different areas of reactivity can be side by side in a single plane or in three dimensions and organic, inorganic, polymeric, metallic or semiconductive materials can be involved which are at least one atom thick. The organic materials can include aliphatic unsaturated and aromatic hydrocarbons, methacrylates, amines, halocarbons, esters, ethers, polymers and others. The inorganic materials can include silicon oxides, titanium oxides, zirconiun oxides, aluminum oxides, platinum oxide, copper oxide and the like as well as mixtures thereof.

"Colloidophilic" is a term used to indicate the preferential attraction of a colloidal particle to these regions of a substrate or film.

Metallic materials useful in this invention include platinum, gold, copper, nickel alloys, palladium, and other materials known for conductive or other purposes.

"Conductive paths" as used in this application are meant to include patterns of all types which may be used as conductors or can be used for other purposes as for example in other electronic uses such as semiconductors or for decorative or other purposes.

Molecular assemblies of this invention can be electrical devices such as printed circuits, semiconductors, capacitors or the like. Electrical devices such as printed circuits have high resolution, good conductivity of metal layers and good adherence of metal layers. Similarly, semi-conductive devices made in accordance with the invention have good resolution and are compatible with standard electrical requirements.

In one embodiment of the invention, selective metallization with high resolution on a silicon substrate is achieved by silanizing a silicon wafer to produce a monomolecular silane layer covalently linked to the substrate with terminal olefin groups which are exposed at the interface. The energy of UV light is of the same order of magnitude as that of covalent bonds and therefore cleavage of covalent bonds into two parts is possible and is known as photolysis. UV light is used in the invention to produce photolysis reactions in the thin films. To that end, the film-coated wafer's surface may be irradiated with X-rays, electon beams, or with deep ultraviolet light (i.e. UV light with wavelengths preferably below 210 nm to achieve the highest possible resolution although longer wavelengths can be used) whose intensity and length of irradiation is sufficient to cleave certain regions of the film. Without subjecting the wafer to an intermediate development step after irradiation, the wafer's surface is then coated with a colloidal palladium-tin (Pd/Sn) catalyst precursor which adheres only to those regions of the film that had not been irradiated. Upon subsequent immersion of the wafer in an electroless plating bath, metal is deposited only in those regions activated by the Pd/Sn catalyst.

A principal feature of the invention, as schematically indicated in FIG. 3A, is the adherence of the colloidal palladium/tin (Pd/Sn) catalyst precursor to the substrate only in those regions that are to be plated in the electroless bath. Once the catalytic layer is formed in the desired pattern, the remainder of the electroless plating procedure, schematically indicated in FIG. 3A, is straightforward. A typical electroless plating process can be found in J. Henry, Metal Finishing Guidebook Directory, Vol. 86, pg. 397–414 (1988). In one aspect the invention resides in interposing a thin film between the substrate and the catalytic layer in a manner such that the thin film is strongly adherent to the substrate and the catalyst is selectively adherent to a high resolution pattern formed in the film.

There are numerous classes of substances whose molecules, under appropriate conditions, self-assemble to form thin films which can act as spacers. In general, those self-assembling molecules characteristically include a polar end, a non-polar opposite end with a reactive moiety at or near the terminus, and an intermediate region typically composed of saturated or unsaturated hydrocarbon chain or may not have an intermediate region as in UTF4. The spacer can be monomeric or polymeric.

The class of polar end groups (which interact with the polar surface of the substrate) include silanes of the $R_nSiX_m$ type where R is an organic functional group;
n is a number between 1, 2 or 3;
m = 4 − n; and
X is a halogen, alkoxy or amines.

The class of polar end groups further includes carboxylic acids, acid chlorides, anhydrides, sulfonyl groups, phosphoryl groups, hydroxyl and amino acid groups.

The class of non-polar end groups include olefins, acetylenes, diacetylenes, acrylates, aromatic hydrocarbons, methacrylates, methyl, perflourinated hydrocarbons, primary amines, long chain hydrocarbons and esters.

Substrates that either intrinsically possess or are treated to have polar functional groups at the surface include silica (quartz and glass), silicon (doped and undoped), other semiconductors (e.g., germanium, gallium arsenide) or organic polymers such as epoxy or polysulfone, metals, and metal oxides such as alumina. The bifunctional molecules may be anchored to the substrate by a variety of procedures involving chemical, photochemical, catalytic, or other reactions.

Thus as described above, the outer layer of the substrate which forms the monomolecular layer which can be identical and integral with the body of the substrate or a separately applied film of a different material, can be polar or non-polar depending on the particular application.

The self-assembling thin film procedure utilized in the invention produces a uniform ultra-thin (less than about 200 nm) monomolecular film having externally accessible reactive groups. Various methods can be employed to alter the reactivity of those groups. The choice of method may be determined in part or in whole by the desired resolution of the pattern to be produced in the film. Among the various methods is the method of making the substrate unreactive or less reactive by photolytic cleavage at the monomolecular structure. As a corollary olefins could be made more reactive to certain coupling agents (such as appropriately modified biomolecules, catalysts, and spectroscopic probes) by oxidation to produce hydroxyl groups. Alteration of reactivity in predetermined regions of the thin film allows chemical reactions to occur either (1) only in those regions whose reactivity has been altered, or (2) everywhere except the altered regions. Consequently, an important attribute of the invention is the ability to produce, with high resolution, sites in the film of different chemical reactivity such that only the reactive moieties are receptive to adhesion by a catalytic precursor to an electroless plating bath.

Where the substrate is a semiconductive wafer of silicon (which can be p-type, n-type, or intrinsic silicon), the film can be produced by a monomolecular layer of a silane of the self-assembling kind. Examples of that kind of silane include but are not limited to 7-octenyldimethylchlorosilane, 5-hexenyldimethylchlorosilane, and other chlorosilanes, and other known silicon materials, methoxysilanes, polysiloxanes, ethoxysiloxanes, 4-aminobutyldimethylmethoxysilane and 1,1,1,3,3,3-hexamethyldisilazane. The films are anchored to the silicon substrate by chemical and physical adsorption, which may involve siloxane (Si-O-Si) bridges and Van der Waals forces. Any substrate having a terminal ionizable hydroxyl group at the surface can provide an anchorage for the silane film. This procedure of using self-assembling monolayers involves covalent bond formation between the monolayer and the substrate whereby the film adheres to the substrate more strongly than physisorbed Langmuir-Blodgett films.

Referring now to FIG. 1A, there is schematically shown the formation of a self-assembling monolayer of silane on a solid substrate by adsorption of silane molecules from a silane solution onto the surface of the solid substrate. In that schematic drawing, the silane molecule is represented as having a "polar" head at one end joined by a hydrocarbon chain to a non-polar functional group situated at the other end of the molecule. The tail can have a reactive or unreactive moiety as shown on the left and right side respectively of FIG. 1A. As schematically indicated in FIG. 1B, where the non-polar functional group has a reactive moiety, that terminal group is symbolized by a triangle; where the terminal group has an unreactive moiety, the group is symbolized by an asterisk. The spacer can be any material that joins the head and tail which can include aliphatic or aromatic, linear or branched chain hydrocarbons which can contain heteroatoms and can have for example up to 20 carbon atoms.

Figure 5A:
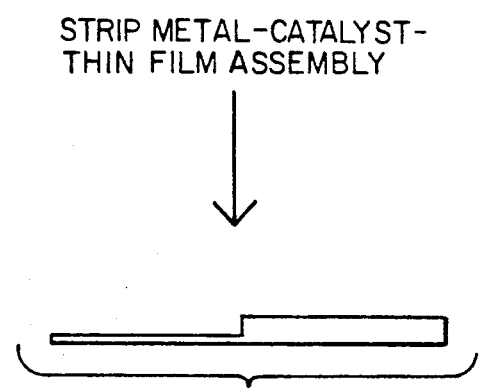
Figure 5B:
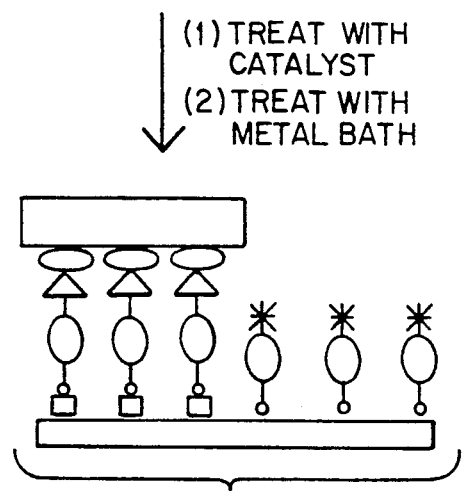

By irradiating selected regions of the silane monolayer with UV light, in the manner indicated in FIG. 2, the reactive moieties at the irradiated silane molecule undergo photo-induced cleavage. When the Pd/Sn colloidal catalyst, as schematically indicated in FIG. 3A and 5B, is spread over the surface of the wafer, the colloidal catalyst binds only to the moieties at the interface that it is adherent to. The catalyst does not adhere to the groups whose reactive moieties were inactivated by exposure to the radiation or moieties such as UTF4 to which the colloid does not adhere well. When the wafer is immersed in an electroless plating bath, plating occurs, as depicted in FIG. 3A, only where the Pd/Sn catalyst precursor is adherent to the silane monolayer. On subjecting the metal patterned substrate to an ion etch, metal topped plateaus remain after the etch, as schematically depicted in FIG. 4A. Oxidizing acid can be used to strip the metal coatings. Known masking and etching steps, procedures and materials in the semiconductor microlithography and printed circuit field as for example described in background above, can be used in this invention.

EXAMPLE 1

An n-type silicon wafer (obtained from Monsanto, St. Louis, MO.) having a native oxide surface was cleaned by standard techniques. After cleaning, wettability of the surface by triply-distilled water was determined, using a Zisman type contact angle goniometer, to be 0°, indicative of an extremely hydrophilic surface (i.e. the surface was wet by the water which spread and formed a film upon the surface). A 1% (v/v) solution of 7-octenyldimethylcholorosilane (UTF1): Petrarch Co., Bristol PA) in toluene at room temperature was applied to the surface of the silicon wafer for a time (e.g., 15 minutes) sufficient to enable a monomolecular film of the UTF1 to be chemisorbed onto the silicon. Residual solvent was removed from the film by baking the wafer on a hot plate for 5 minutes in air at a temperature of about 100° C. The silanized surface was very hydrophobic (i.e. repellant to water), giving a contact angle with water of 85°.

XD2408-T palladium chloride/tin chloride colloidal activator (MacDermid Co., Waterbury, CT) was used as received. The silanized wafer surface was covered by the Pd/Sn colloidal activator for five minutes. The wafer was then rinsed copiously with water. The surface of the wafer was clearly hydrophilic, indicative of the bonding of the colloid. The wafer was then immersed for five minutes in a Metex 9027 electroless copper plating bath prepared in accordance with the manufacturer's (MacDermid) directions. The wafer, after removal from the bath, was thoroughly rinsed with water. A copper metal coat was visible over the surface of the wafer. Examination of the surface of the wafer using a scanning electron microscope revealed the presence of a uniform, continuous metal coat on the wafers surface.

EXAMPLE 2

The entire procedure specified in Example 1, except for the omission of the step of silanizing the surface of the wafer with UTF1 and an increase of the time in the plating bath was repeated using a similar n-type silicon wafer with a native oxide surface (obtained from Monsanto). After 15 minutes immersion in the electroless copper plating bath only a few small, randomly distributed patches of metal were present on the wafer surface.

EXAMPLE 3

An n-type silicon wafer with a native oxide surface (obtained from Monsanto) was silanized using the procedure described in Example 1. The wafer was then placed in an argon atmosphere and irradiated for 10 minutes with ultraviolet light from a mercury/argon lamp (Oriel Co., Stamford CT) that was spaced at a distance of 3 cm from the wafer. The intensity of the radiation, as measured with a Mamir UV dosimeter at 254 nm was 4.3 mW/cm$^2$ at 3 cm from the irradiated surface of the wafer. After being immersed for 15 minutes in the copper plating bath employed in Example 1, no copper plate was present on the wafer.

EXAMPLE 4

An n-type silicon wafer with a native oxide surface (obtained from Monsanto) was cleaned by standard techniques and was then silanized using the procedure described in Example 1. After the residual solvent had been driven off the wafer was allowed to cool to room temperature. A low resolution metal mask was placed in mechanical contact with the silanized surface to block the light in selected regions. The wafer was then flood irradiated for 10 minutes by ultraviolet (UV) light from a mercury/argon (Hq/Ar) lamp (Oriel Co, Stamford, CT) while the wafer was situated in an inert gaseous atmosphere of argon. The intensity of the UV radiation, as measured with a Mamir UV dosimeter, was 4.3 mW/cm$^2$ at 3 cm from the surface of the wafer and the measured wavelength of that UV radiation was 254 nm. After exposure to the UV radiation, the wafer surface was immersed in the XD2408-T palladium chloride/tin chloride colloidal activator (MacDermid Co.) for five minutes. The wafer was then thoroughly rinsed with water. Only the regions of the surface that had not been irradiated were hydrophilic. That result indicated that the olefinic silane interacted strongly with the Pd/Sn colloid. Subsequent immersion of the wafer into the Metex 9027 Cu bath for five minutes, as in Example 1, produced a thin copper plate that reproduced the features of the masked regions When the mask used has many patterns of metal depositions, the lines of metal can be very close together with high resolution and well defined non metal areas.

EXAMPLE 5

An n-type silicon wafer with a native oxide surface was silanized using the Example 1 procedure except that a 2% (v/v) solution of the UTF1 silane in toluene was used. The silanized wafer was irradiated for 15 minutes through a photolithograph mask having an electron beam defined chrome film on a quartz blank. Prior to silanization of the wafer, a Pd/Sn colloidal activator had been prepared from Cataposit 44 concentrate and solid Cataprep 404, as directed by the manufacturer (Shipley Company, Newton, MA). An electroless copper plating bath had also been prepared from 328A and 328Q stock solutions as prescribed by the Shipley Company which manufactured those stock solutions.

After irradiation, using the photolithography procedure, the wafer was covered by the Shipley colloid for five minutes. After a thorough rinse with distilled water, the wafer was immersed in the copper plating bath for two and one half minutes. After rinsing the wafer, the wafer surface was inspected by bright field reflectance microscopy. That inspection showed that the pattern of the mask had been reproduced in copper on the wafer. The thickness of the copper film, measured with a Sloan Dektak profilometer, was 20 nm. The conductivity of the film was 5000 mho/cm as measured with a two-point probe apparatus.

The copper patterned wafer was placed in a Plasmatherm Model 54 reactive ion etch system (Plasmatherm Co., Crescent, N.J.) and exposed to $CF_4^+$ plasma for five minutes. Under the prevailing conditions, the etch rate of the silicon substrate was 0.1 microns/min, giving a total etch of 0.5 microns. Examination of the wafer with a Nikon Optiphot M differential interference contrast Nomarski microscope revealed that the wafer had been etched to a depth of 0.5 microns everywhere except beneath the copper plating. Lines five microns in width with five micron spacing between adjacent lines (the resolution of the edges was about 1 micron), as well as other patterns, had been reproduced on the silicon wafer as raised regions above the etched surface, i.e. as plateau regions. It was evident that the copper pattern had served as a high resolution, positive resist layer. Examination of the etched wafer by X-ray fluorescence line scan in an ISI Scanning Electron Microscope equipped with a Kevex energy-despersive, X-ray spectrometer, showed that copper was still present in the raised areas and proved that the copper plate had survived five minutes in the ion plasma.

EXAMPLE 6

A copper patterned n-type silicon wafer was produced using the Example 5 procedure. However, a different photolithograph chrome on quartz mask having micron-sized features was employed for patterning. Before subjecting the copper patterned silicon wafer to the $CF_4^+$ plasma etch, a microscopic examination of the wafer revealed excellent reproduction of the mask pattern in copper on the surface of the wafer. After plasma etching the wafer for five minutes, the wafer was removed from the etching apparatus and was then examined with an electron microscope. The resistance of the copper plate to the plasma etch was apparent in the metallized regions where copper of approximately 40 nm thickness remained in the raised regions Among the features reproduced on the wafer were lines about one centimeter long and less than 2 microns wide, lines 4 microns long and about a half micron in width, and a square cavity (i.e. a "trough") about five microns on a side.

EXAMPLE 7

The procedure of Example 4 was repeated using a p-type silicon wafer (obtained from Monsanto). As in Example 4, a thin copper plate was formed on the wafer that reproduced the features of the masked regions. No appreciable difference was discerned between the plate on the p-type wafer and the plate on the n-type wafer.

EXAMPLE 8

The procedure of Example 1 was repeated using a 1% solution of 5-hexenyldimethylchlorosilane (UTF2; Petrarch Co., Bristol PA) in toluene. The wafer was irradiated and then plated with copper as in example 5. There was no apparent difference between the metal pattern produced on the UTF2-treated surface and the UTF1-treated surface.

EXAMPLE 9

This example shows patterning of polycrystalline silicon (polysilicon) using 4-aminobutyldimethylmethoxysilane (UTF3).

Polysilicon is the material that is most commonly used to define gate and interconnect structures at the highest resolution required for microcircuit fabrication UTF3 is a surface silanizing reagent similar to 7-octenyldimethylchlorosilane (UTF1) and 5-hexenyldimethylchlorosilane (UTF2) in that the polar end of the molecule reacts with hydroxyl groups on the surface of the substrate. UTF3, however, liberates $CH_3OH$ instead of HCl as a byproduct of the surface reaction. UTF3 also differs from the other two silanes in that the nonpolar end has a terminal primary amine group instead of an olefin. It is known in the electroless plating industry that amino groups are attractive for binding the Pd/Sn colloidal catalyst prior to metal deposition. The use of amino groups on a silicon surface provide an alternative to olefin groups for high-resolution metal patterning.

A p-type silicon wafer had 4000 angstroms of polysilicon deposited on it by chemical vapor deposition with a Bruce 735 furnace at 625° C. The wafer was then cleaned by standard procedures. The contact angle was zero degrees. The wafer was treated by immersion in a 2 percent (v/v) solution of UTF3 in toluene under argon atmosphere for 5 minutes. The wafer was baked at 100° C. for 2 minutes on a hot plate and the contact angle was measured and found to be 76 degrees. The treated wafer was cut into two halves, one of which was exposed to a colloidal Pd/Sn activator for 5 minutes. The colloid was removed and the wafer was washed with distilled water The wafer was then placed in an electroless copper plating bath for 2 minutes. A continuous film of copper was formed on the wafer. This result demonstrated that the primary amine is another example of a surface-immobilized functional group (in addition to the above-mentioned olefin groups) that can bind the colloidal Pd/Sn and subsequently catalyze metal deposition. The other half of the wafer was irradiated through a mask for 30 minutes with a Hq/Ar pen lamp at a distance of 2 cm. The wafer was then plated with a smooth, continuous film of Cu which developed only in the areas that were masked.

EXAMPLE 10

An excellent method of obtaining molecular information about ultra-thin films is by the use of infrared spectroscopy with an attenuated total reflection (ATR) cell to provide signal amplification. A 45° silicon crystal (Harrick Co., Ossining NY) was treated with UTF1 as described in Example 1. The crystal was held in a Wilks Scientific 9000 ATR cell and scanned 16000 times under nitrogen atmosphere from 4000 $cm^{-1}$ to the crystal cutoff at 1500 $cm^{-1}$ using a P-E 1800 spectrophotometer. The resulting spectrum was corrected by subtraction of the spectrum of the clean, untreated crystal. Peaks due to the hydrocarbon region of UTF1 film were observed and assigned as follows: 2854 $cm^{-1}$ (symmetric $CH_2$ stretch), 2924 $cm^{-1}$ (asymmetric $CH_2$ stretch), 2956 $cm^{-1}$ (asymmetric $CH_3$ stretch), 2998 $cm^{-1}$ (symmetric $CH_3$ stretch), and 3078 $cm^{-1}$ (vinyl stretch). Essentially identical peaks were observed in the spectrum of the neat UTF1 liquid spread between two KRS-5 plates (Wilks Scientific). Peaks were observed at 3077 $cm^{-1}$, 2996 $cm^{-1}$, 2956 $cm^{-1}$, 2927 cm$^{-1}$ and 2857 cm$^{-1}$. The slight shift to lower energies and the narrower peak width in the monolayer spectrum indicates that the monolayer is more ordered than the neat liquid.

The film was then irradiated with a Hg/Ar lamp for 30 minutes. The background-corrected spectrum of the crystal after irradiation was featureless, indicating cleavage of the monolayer from the surface. This observation suggests that it is possible to replace a photochemically cleaved molecule with a different molecule at that site, giving greater flexibility in the types of chemically-reactive moieties that could be patterned at high lateral resolution.

EXAMPLE 11

Fabrication of high-resolution copper patterns on alumina ($Al_2O_3$).

A highly-polished, microwave-quality alumina ($Al_2O_3$) wafer (E.I. Dupont de Nemours Co.) was cleaned by the standard procedure (contact angle 0°) and then treated with UTF1 as in Example 1 (contact angle = 82°). The plate was subjected to masked irradiation for 30 minutes with a Hg/Ar lamp. The wafer was plated for four minutes using the standard copper plating procedure and then rinsed with water. Copper was deposited only in the masked areas. The resistance of the copper layer was measured using a two-point probe technique and found to be less than 0.1 ohms/cm, indicating that the copper films were continuous and highly conductive. The adhesion of the copper patterns was tested by pressing scotch tape down on the alumina plate and then peeling it off. No copper came off onto the tape and it did not lift off the surface of the alumina even after several repeated attempts This demonstrates that the process can be used to fabricate high-resolution, adherent metal patterns on ceramic substrates such as alumina which can be used for production of microwave communication circuitry.

EXAMPLE 12

Fabrication of metal patterns on silicon nitride ($Si_3N_4$). Silicon nitride is a commonly used dielectric material in silicon microcircuit fabrication.

A one-half micron thick film of silicon nitride was deposited onto a p-type silicon wafer. The wafer was cleaned using a standard procedure and treated with UTF3 using the procedure of Example 9 (contact angle = 62°). The wafer was irradiated for 30 minutes with a Hg/Ar lamp through a single-level chrome-on-quartz transistor mask. Vacuum contact to the mask was made with a SUSS MJB 3 contact aligner. The patterned film was metallized using the standard copper plating procedure, revealing features with linewidths as small as 0.5 micron structures.

This result demonstrates that silicon nitride is another substrate that is amenable to high-resolution metal pattern formation using the new process with a commercially available contact aligner. The contact aligner system provides improved mask-substrate contact in contrast to the mechanical contact method described in Example 4. Improved contact reduces certain optical aberrations such as shadowing and diffraction and will allow formation of higher resolution patterns.

EXAMPLE 13

Fabrication of metal patterns on chemical vapor deposited silicon oxide (CVD oxide). CVD oxide is a commonly used dielectric material in silicon microcircuit fabrication.

A one-half micron thick layer of CVD oxide was deposited on p-type silicon in a chemical vapor deposition furnace at 300° C. The wafer was cleaned and treated with UTF3 as in Example 9 (contact angle = 76°), and high resolution copper patterns were fabricated on the wafer using the exposure and plating procedure described in Example 12.

This result demonstrates metal patterns can be formed on CVD oxide using the claimed process.

EXAMPLE 14

Fabrication of metal patterns on thermally-grown silicon dioxide (thermal oxide). Thermal oxide is a commonly used dielectric material in silicon microcircuit fabrication.

A 50 nm thick layer of thermal oxide was grown on n-type silicon in a Thermco model 201 furnace at 1000° C. High resolution copper patterns were fabricated on the wafer using the procedure described in Example 12.

This result demonstrates metal patterns can be formed on thermal oxide using the process of this invention.

EXAMPLE 15

Fabrication of high resolution metal patterns on quartz.

A quartz slide (ESCO Products) was cleaned and treated with UTF1 as described in Example 1 (contact angle = 78°). The film was patterned and metallized as described in Example 4. Continuous copper patterns were observed with linewidths down to 1 micron.

This result demonstrates that high resolution metal patterns can be formed on quartz, showing that masks for microlithography can be fabricated using this new procedure.

EXAMPLE 16

Fabrication of high-resolution metal patterns on p-type silicon using an argon fluoride (ArF) excimer laser as the source.

P-type silicon wafers were cleaned and treated with UTF1 as in Example 1 (contact angles varied between 80–85 degrees). The films were irradiated through a high resolution mask (mechanical contact) with a Lambda Physik model 103 ArF excimer laser which emits at 193 nm. The beam was a 0.8 cm × 3.0 cm rectangle. The beam intensity was measured before and after each irradiation with a Scientech model 365 power energy meter and thermopile detector. The pulse rate for all irradiations was 4 Hz. The films were exposed to total dosages of 11.5, 23, and 46 J/cm$^2$ using a pulse intensity of 23 mJ/cm$^2$, and to total dosages of 1.5, 3.1, 11.5, 23, 46 and 92 J/cm$^2$ using a pulse intensity of 20.8 mJ/cm$^2$. The films were metallized using the standard plating procedures in Example 5. High resolution copper patterns were formed on the wafers with features as small as 0.6 microns for all values of total dosage and pulse intensity used. However, the minimum amount of extraneous deposited metal was observed at dosages of 11.5 J/cm$^2$. Dosages of 23 J/cm$^2$ or more resulted in a considerable amount of undesired plating which became more severe with increasing total dosage.

This result demonstrates that 193 nm light can be used to pattern UTF1 and that the approximate dosage window is 10-20 J/cm$^2$ or less at pulse intensity of about 20-23 mJ/cm$^2$.

EXAMPLE 17

Fabrication of high resolution metal patterns on alumina using an ArF excimer laser as an irradiation source.

An alumina wafer was cleaned and treated with UTF1 as described in Example 11. The film was irradiated with a pulse intensity of 20.8 mJ/cm$^2$ with total dosages of 40, 20, 15, and 10 J/cm$^2$. The film was then selectively metallized with copper to give high resolution metal patterns with line widths down to one micron. As in Example 16 with the silicon substrate, the higher total dosages of 20 and 40 J/cm$^2$ showed evidence of extra plating but the lower dosages gave very little or no extra plating.

This result demonstrates that the dose required for patterning is not a function of the substrate on which the film is attached.

EXAMPLE 18

Fabrication of high-resolution metal patterns on chemical vapor deposited (CVD) oxide with an ArF excimer laser.

P-type silicon wafers, with a one-half micron thick layer of CVD oxide were treated with UTF3 as described in Example 12. The film was patterned with masked irradiation from an ArF excimer laser as described in Example 16, with the exception that the pulse intensity was considerably lower. A pulse intensity of 0.45 mJ/cm$^2$ at 15 Hz was used to give a total dosage 13.8 J/cm$^2$. The wafer was then metallized with the standard copper plating procedures used in Example 9. High-resolution (0.5 micron linewidth) metal patterns were formed on the wafer.

This result demonstrates that lowering the pulse intensity by two orders of magnitude and increasing the pulse rate has no apparent effect on the total dosage window. It also shows that the dosage window for UTF3 is essentially the same as for UTF1 using 193 nm light.

EXAMPLE 19

Fabrication of high-resolution metal patterns on polysilicon with an ArF excimer laser.

P-type silicon wafers with a one-half micron thick layer of polysilicon were treated with UTF3 as described in Example 9. The film was patterned and metallized as described in Example 18, with the exception that a pulse intensity of 0.29 mJ/cm$^2$ at 20 Hz was used to give a total dose of 12 J/cm$^2$. High-resolution patterns were developed with line widths as small as 0.5 microns.

This result demonstrates that the substrate has no effect on the dosage requirements for patterning of UTF3.

EXAMPLE 20

Fabrication of high-resolution metal patterns on polysilicon using a commercial ArF laser/alignment system.

Twelve p-type silicon wafers with a 30 nm thick layer of thermally-grown silicon dioxide (gate oxide layer) and a 350 nm thick top layer of n-type polysilicon were deposited and cleaned by the standard procedure. Wafers 1–6 were treated with UTF1 as described in Example 1; wafers 7–12 were treated with UTF3 as described in Example 9. The treated wafers were patterned one week after film formation and storage in polypropylene wafer carriers. The wafers were exposed by an ArF laser through a fused silica NMOS transistor mask coupled with a SUSS MA 56 5-inch production mask aligner. All irradiations were done with a pulse intensity of approximately 0.27 mJ/cm$^2$ at a pulse rate of 150 Hz. Total dosages were 8-20 J/cm$^2$, requiring 200–500 seconds of elapsed time to complete the exposure. The contact pressure was varied from hard vacuum contact to soft contact of 900 g/wafer and 500 g/wafer. The wafers were metallized with the standard copper plating procedure. Essentially all (>90%) of the patterns present on the mask were replicated on the wafers where vacuum contact was employed, however a substantial amount of metal was deposited in other areas of the wafer as well. This effect is probably due to destructive interference reflection inherent in monochromatic collimated light sources. The deposition of metal in undesired areas was reduced or eliminated by using softer contact to the mask, but replication of the highest resolution (sub-micron) features was poorer.

This result demonstrates the utility of a commercial source/alignment system in the fabrication of high-resolution metal patterns on a semiconductor substrate. It also shows that UTF1 and UTF3 can both be used to make metal patterns despite the difference in the nature of the reactive group at the non-polar end of the molecule and that the two films have the same dosage window. The energy required to pattern the resists—on the order of 10 J/cm$^2$—is considerably higher than values for conventional thick film photoresists which are approximately 10-100 mJ/cm$^2$. As a result, the time required for patterning of the UTF films is much longer for a given energy dosage. However, new ArF laser projection systems have been developed that provide pulse intensities of 1.0 J/cm$^2$ at 150 Hz (D.J. Ehrlich, J.Y. Tsao and C.0. Bozler, *Journal of Vacuum Science and Technology B*, vol. 3, pg. 1, 1985). The total elapsed time required to pattern a UTF film with such a system would be approximately 0.07 seconds. This value is well within the 1.0 second guideline for exposure time required for VHSIC production lines to give a wafer throughput of 60/hr.

EXAMPLE 21

Fabrication of NMOS transistor test structures using a commercial ArF laser/alignment system.

Wafer 6, with copper transistor test patterns fabricated as described in Example 20, was placed in a Plasma Therm 500 reactive ion etcher (RIE) using 150 millitorr of freon 115 TM at a flow rate of 50 cc/min and a plate power of 150 W. This resulted in removal of the 350 nm thick polysilicon layer except from areas that were protected by the copper overlayer. The copper was removed by dipping the wafer in 18 molar nitric acid for 2 minutes and rinsed with distilled water. Sources and drains were fabricated by doping the wafer with phosphorus using a model 300 kV Excelator ion implanter operated at an energy of 75 Kev to a dosage of $2 \times 10^{15}$ ions/cm$^2$. The implanted wafer was cleaned using the RCA TM cleaning process with a 40 second buffered hydrofluoric acid etch (to remove the thermally-grown gate oxide layer), then heated to 900° C. in a nitrogen atmosphere.

The electrical properties of the single-level transistor test structures were evaluated using the two-point probe method using two micromanipulators in conjunction with a Tectronix model 576 curve tracer. No discontinuities were found on all lines tested. The currentvoltage responses of 10 micron, 5 micron, and 1 micron wide gate structures were measured and gave the behavior expected of working transistors. The wafer was examined by SEM and showed continuous 0.5 micron polysilicon gates with vertical edges and no evidence of pinholes.

This result demonstrates the ability to strip the copper resist after etching and that replication of the mask structures in the etched substrate is extremely accurate It demonstrates that reactive ion etching using freon 115 TM can be used to transfer the metal patterns into the substrate with very high edge acuity compared to conventional organic photoresists. This example shows that the silane film on the substrate is extremely stable since the film was put on the wafers one week before the patterning operation was performed. Finally, the example demonstrates the fabrication of working high-resolution transistor test structures using the new process. It also demonstrates that other important components of integrated circuits, such as interconnects, vias, contacts and capacitors could be produced using this process.

EXAMPLE 22

Fabrication of metal patterns in a negative image.

An n-type silicon wafer with a one-half micron thick layer of CVD oxide was cleaned and subsequently treated with neat 1,1,1,3,3,3-hexamethyldisilazane (UTF4) for 20 minutes (contact angle=79°). The wafer was then cured for 3 minutes at 100 degrees centigrade. Reaction of UTF4 with the substrate produces a surface of trimethylsilyl groups with the concomitant liberation of ammonia. The film was patterned with a low resolution mask and Hg/Ar lamp; the exposure was 30 min. The contact angle in the unirradiated areas remained the same but decreased to 0° in the irradiated areas. The patterned wafer was then treated with UTF3 as described in Example 9 whereupon the contact angle in the previously irradiated areas increased from 0° to 64°. The wafer was then metallized using the standard copper plating procedure. Metal pattern formation was observed only in the irradiated areas of the wafer, i.e., development of a negative image.

This is the first example of negative image formation by the new process. This result demonstrates that irradiation of UTF4 creates regions on the substrate that are amenable to attachment of a second silanizing reagent Since the surface reaction requires the presence of hydroxyl groups, it is highly likely that irradiation causes cleavage of the initial monolayer from the surface at the Si-O or Si-C bond, revealing exposed areas of the bare substrate. Therefore, any chemical reaction that involved hydroxyl groups (such as silanization) can be performed in the irradiated areas. This result also shows that UTF4 is useful as a reagent to prevent metal deposition in selected regions.

EXAMPLE 23

Fabrication of metal patterns using a two-stage surface activation system.

An n-type silicon wafer with about one-half micron of CVD oxide was cleaned and then treated with UTF3 as described in Example 9. The film was patterned with a low resolution mask and exposed with a Hg/Ar lamp for 30 min. The wafer was then treated for 3 minutes with a solution containing 10 g/L $SnCl_2$ in 0.5 M HCl, rinsed three times with distilled water, then treated for 3 minutes with a solution with 0.25 g/L of $PdCl_2$ in 0.05 M HCl and rinsed again. The wafer was then metallized using a standard copper plating bath to produce a very smooth copper film in the unirradiated areas of the film. Upon observation by optical reflection microscopy, the plated film appeared to be smoother than the copper coatings produced using the commercial catalytic Pd/Sn activators described in previous examples.

This result demonstrates that a two-stage tin and palladium activator system can be used to produce improved copper coatings. It is possible to use alternate deposition schemes as well.

EXAMPLE 24

Fabrication of MOS capacitor test structures.

An n-type silicon wafer with a 100 nm thick thermal oxide layer was cleaned and treated with UTF3 as in example 14. The film was patterned using a mask with standard capacitor test structures and irradiated for 28 minutes with an Hg/Ar lamp. The wafer was metallized with the standard copper plating procedures, used in Example 5, yielding metal squares 800 microns on a side (area=$6 \times 10^{-3}$ cm$^2$) The metal/thermal oxide/n-type silicon (MOS) capacitors were then characterized by probing the metal pads and the back of the wafer with a Micromanipulator automatic C-V measuring system. The capacitance was found to be 26 pF/cm$^2$ with minimal (10 mV) hysteresis and remained stable at room temperature for at over 3 weeks, indicating that device degradation due to masked metal contamination (diffusion of copper into the thermal oxide) was not a problem.

This is a demonstration of functional metal/dielectric/semiconductor capacitors produced by the new process.

EXAMPLE 25

Demonstration of step coverage on polysilicon

A 400 nm thick layer of p-type polysilicon was deposited onto a n-type silicon wafer that had previously been covered with a series of parallel CVD oxide lines that were 10 or 20 microns wide and 400 nm thick. The wafer was then cleaned and treated with UTF3 as described in Example 9. The film was patterned by irradiation for 28 minutes with a Hg/Ar lamp using the same parallel line mask oriented at 90° to the CVD oxide lines. The film was metallized using the standard copper plating procedure. The resulting copper lines were found to be continuous, of uniform thickness and accurately followed the contours of the polysilicon steps.

This result demonstrates excellent step coverage which is important in the fabrication of gates and interconnects in non-planar regions of the wafer.

EXAMPLE 26

Fabrication of metal patterns on platinum.

Platinum foil was cleaned by flaming with a propane torch until it glowed orange. The contact angle of the clean foil was 0°. The foil was then treated with UTF3 and patterned with low-resolution features as in Example 9. The contact angle of the unirradiated areas was 73°; the irradiated areas gave a contact angle of 0°. The patterned film was metallized using the standard copper plating procedure. Metal pattern development was observed only in the masked areas and displayed excellent adhesion to the substrate, as demonstrated by the scotch tape test described in Example 11.

This result demonstrates fabrication of metal patterns on metal substrates that have a thin surface oxide.

EXAMPLE 27

Fabrication of high-resolution patterns on a GaAs substrate coated with $Si_3N_4$.

A gallium arsenide substrate was coated with a 100 nm thick layer of silicon nitride using a plasma deposition process. The contact angle of the plasma nitride layer was 0°. The wafer was treated with UTF3 (contact angle=73°), patterned using a mask and metallized as described in Example 12. Continuous metal lines that replicated the mask features were produced on the substrate.

This shows that the plasma nitride/GaAs assembly can be used as a substrate for high-resolution metal pattern formation on a semiconductor other than silicon.

EXAMPLE 28

Selective metallization of trichloro(4-pyridyl)-ethylsilane.

An ultrathin film of this material was prepared on a clean glass slide using standard procedures that have been described for the other silane materials. The contact angle was found to be about 40°. The film was exposed to masked irradiation from a mercury/argon pen lamp which was passed through a 7-43 bandpass filter (Corning Glass Corp.) This filter passes wavelengths only between 235 nm and 415 nm, and does not transmit any other wavelengths of the pen lamp, such as the 195 nm and 185 nm lines, that are known to be involved in photochemical reactions of the films.

The film was irradiated for 90 minutes, as opposed to the nominal 30 minutes used for unfiltered irradiations. The extra time was allotted because the filter only passes about 35% of the incident light at 254 nm, a wavelength that is probably important for the photochemical pattern definition with the pyridinyl film.

After irradiation, the film was processed through the standard plating sequence, using chemicals from Shipley Co. Metal pattern formation was observed preferentially in the masked regions of the film-coated substrate. This indicates that the presence of a moiety in the film such as the pyridyl group that can absorb light at longer wavelengths than an isolated olefin, endows the film with photosensitivity at those longer wavelengths. This allows the use of currently available sources (e.g., krypton fluoride (248 nm) excimer laser steppers or conventional mercury lamps) rather than argon fluoride (193 nm) laser steppers to provide the pattern definition. The development of a pattern at the dosage employed here indicates that the sensitivity of the film is at least comparable to the other silanes (because the same total dosage was employed).

EXAMPLE 29

A polysulfone board (Victrex PES3601MG20, LNP Plastics Co.) was exposed to filtered, patterned radiation from a mercury/argon pen lamp as described in Example 28, above. Exposure time was 90 minutes. The board was metallized selectively using Shipley copper plating baths. The aromatic groups in the polysulfone resin can absorb 254 nm radiation. The same implications for irradiation sources described in Example 28 also apply here.

EXAMPLE 30

A clean silicon thermal oxide wafer was placed in a scanning electron microscope (SEM) that had suitable attachments for high-resolution pattern generation. The electron beam was rastered across the surface of the wafer to produce lines of varying width. After irradiation, the wafer was removed from the SEM and metallized selectivity using Shipley plating baths. Copper metal was deposited selectively onto the wafer only in the regions that were exposed to the electron beam. This corresponds o a negative image formation—an extremely attractive feature for E-beam lithography because one generally produces patterns only on a small fraction of the wafer surface, and it is preferable to irradiate only those regions where patterns are to be, rather than everywhere else. Metal lines as fine as 0.1 micron wide were produced using this technique.

The metallization can be achieved after exposure of the wafer to a wide range of electron dosages, up to several hundred millicoulombs per square centimeter. Better results (cleaner patterns) seem to be obtained at relatively low dosages, such as 70 $mC/cm^2$. The resolution achieved in this experiment is probably limited by the size of the electron beam. Much smaller beam widths or low energy (e.g. 15V), high-resolution electron beams can be employed to potentially achieve sub-100 nm linewidths. Another irradiation source could be a scanning tunneling microscope, which has already been shown to be usable as an irradiation tool for E-beam lithography in the 10 nm linewidth regime. (McCord and Pease, J. Vac. Sci Tech. B, pg. 86, 1986).

EXAMPLE 31

This example shows bimetallic patterns (High phosphorus Ni/Cu, Low phosphorus Ni/Cu).

A p-type silicon wafer was treated with UTF1 as in Example 1 and broken into two halves. Both wafers were subjected to masked irradiation for 30 minutes with a Hg/Ar pen lamp. The wafers were treated with MacDermid XD2408-T, Pd/Sn colloid for 5 minutes and then washed with water. One wafer was then placed in a high phosphorus content nickel plating bath (J67/J28R) obtained from MacDermid (Waterbury, CT) for 4 minutes. The other half was plated with a low phosphorus content nickel plating solution (MacDermid J60/J61) for 4 minutes. Both wafers developed high resolution patterns with features as small as one micron. Both wafers were then placed in a copper plating bath. All patterns that were originally silver in color turned to a copper color in two minutes. This result demonstrates that high-resolution patterns can be prepared of both low-P (magnetic) nickel and high-P (nonmagnetic) nickel. It also shows that a patterned metal layer can serve as a substrate for subsequent deposition of other materials such as metals without loss of resolution.

EXAMPLE 32

Selective metallization can be carried out on silane films having aromatic groups bound directly to the silicon atom. Ultrathin films of silanes having aromatic groups bonded directly to a silicon atom were prepared on clean polysilicon surfaces using standard procedures that have been described for the other silane materials. The silanes employed were: chlorotriphenylsilane (CTP), diphenylvinylchlorosilane (DPVC), and p-chloromethylphenyltrichlorosilane (CMPTC). The film-coated substrates were exposed to masked irradiation from a Karl Suss Model MJB3 UV contact aligner using the output from a mercury/xenon 500 W lamp. The radiation from this source that reaches the substrate consists only of wavelengths longer than 220 nm.

The films were irradiated for 30 minutes with the lamp output adjusted to 7mW/cm$^2$ at 254 nm. The wafers were then processed through the standard plating sequence, using chemicals from Shipley Co. A thin (ca. 50 nm thick), continuous metal pattern developed preferentially in the masked regions of the film-coated substrate. In the case of the CMPTC and CTP silane, essentially no plating was observed in the unmasked regions.

As in Example 28, the presence of a moiety in the film such as a phenyl group that can absorb light at longer wavelengths than a group such as an isolated olefin, endows the film with photosensitivity at those longer wavelengths. However, the improved contrast between the plated and unplated regions for the CMPTC and CTP silane, as opposed to the lower contrast observed with the ethylpyridinyl silane used in Example 28 and DPVC, indicates the importance of the position of the aromatic group in the molecule.

The origin of the contrast development, as currently envisioned, involves the absorption of light by a chromophore in the film that causes photolytic cleavage of the molecule at, or in the vicinity, of the chromophoric group. When less energetic radiation, e.g. longer wavelengths than 220 nm, is employed for patterning, chromophores such as phenyl or pyridine rings can be excited but chromophores that do not absorb at these longer wavelengths will not be excited. With films that have chromophores sensitive to this radiation at positions remote from the silicon atom, photolytic cleavage may occur only at that position, leaving attached to the silicon atom organic moieties such as methyl, vinyl and methylene groups The surface therefore has patterns of the original film in the masked areas intermingled with partially cleaved film in the exposed areas. This may be the case with the DPVC film, where the phenyl rings are cleaved and the vinyl group remains. The partially cleaved molecules may still bind the Pd/Sn colloid sufficiently well to cause plating to occur in the exposed areas, although of poorer quality and coverage than in the unexposed regions If films with only aromatic groups directly bonded to the silicon atom are employed, then photolytic cleavage would cause removal of all the organic portions of the molecule at the silicon atom. This would result in an analogous situation to when sub-200 nm radiation is employed, because most organic moieties absorb sub-200 nm radiation and would therefore be cleaved.

EXAMPLE 33

Selective metal plating of p-chloromethylphenyltrichlorosilane can be carried out using a KrF excimer laser as the exposure tool.

Wafers were treated as in Example 32 with the CMPTC silane and exposed through a quartz mask with a KrF (248 nm) Lamda Physik excimer laser. The pulse intensity of the laser was approximately 400 mJ/cm$^2$ and the wafer was exposed for 5 and 7 seconds at a pulse rate of 4 Hz. The total dosage delivered to the wafer was 8.5 J/cm$^2$ and 11.9 J/cm$^2$.

The wafers were then processed through the standard plating sequence using chemicals from Shipley Co. A thin continuous metal pattern with sub-micron features developed preferentially in the masked regions of the film-coated substrate and, essentially no plating was observed in the unmasked regions.

EXAMPLE 34

Selective metallization can be carried out on silane films having aromatic groups bound via a spacer group to the silicon atom. Ultrathin films of silanes having aromatic groups bonded via a spacer group to the silicon atom were prepared on clean polysilicon surfaces using standard procedures that have been described for the other silane materials. The silanes (obtained from Petrarch Co., Bristol, PA) employed were: trichloro-(4-pyridyl) ethylsilane (pyridyl silane), and 7-[3-(chlorodimethylsilyl)propoxy]-4-methylcoumarin (coumarin silane). The film-coated substrates were exposed to masked irradiation from a mercury/argon lamp as in Example 3. The films were irradiated for 30 minutes. The wafers were then processed through the standard plating sequence, using chemicals from Shipley Co. A thin (ca. 50 nm thick), continuous metal pattern developed only in the masked regions of the film-coated substrates.

While the theory of operation of the invention is uncertain, it is believed that the radiation acts to remove at least organic groups present on the surface of organic substrates where they are used For example, in Example 10, the infrared spectra of silane monolayer films after radiation with deep UV light showed that the organic groups (e.g., methyl groups, octenyl groups) were no longer detectable It is believed that at least the organic groups were removed from the film in the irradiated areas either by photolytic cleavage of the Si—C and/or Si—O—(surface) bonds and possibly C—C bonds as well. It is believed that although organic parts are removed from the silane film by radiation, a significant amount of the silicon from silane deposit remains on the surface after radiation and it is theorized that photolytic cleavage occurs preferentially at the Si—C and C—C bonds rather than at the Si—O bonds and further that at least a partial atomic layer of silicon oxide is left after irradiation Because of the known reactivity of freshly cleaved or sputted Si, the photolytic product likely reacts rapidly with an ambient atmosphere to produce surface Si—OH and/or Si—O groups. It can be demonstrated that the silicon oxide can be built up selectively with atomic resolution in the Z direction and sub-micron resolution in the XY directions (where X and Y are in the plane of the film and Z is perpendicular to the substrate). It is expected that one could build patterned molecular assemblies of silicon oxides by successive film deposition and photolytic cleavage steps. Therefore, one could fabricate silicon based semiconductive microcircuits using a bottom up approach, eliminating the need for any etching steps. Similarly, the mechanism operative for silane films could be operative for titanites, zirconates, and aluminates such that molecular assemblies consisting of titanium oxides, zirconium oxides, aluminum oxides and related surface reactive agents or combinations of these can be built up selectively.

While the metal layer is the preferred material for patterning and deposition as for use in printed circuits and the like, the layer to be applied to the substrate can be of inorganic materials, organic materials, semiconductive materials, metals or combinations thereof. While a layer is preferably provided independently over and adherent to a substrate, which layer is a radiation reactive material, as for example by the use of a silane on an organic substrate, in some cases, the surface of the substrate can itself be considered a layer of radiation reactive material.

While it is preferred that a self-assembling monomolecular film be chemically absorbed on the surface of a substrate having functional groups, in some cases, the film can be formed or considered a part of the outer surface of the substrate. Thus, if a substrate has a chromophore embodied in it, that is a material which absorbs the wavelength to which it is exposed and changes its receptivity to electroless plating from receptive to metal plating to not receptive to metal plating or vice versa, that substrate can be used directly without an additional monomolecular film being formed thereover. In all cases, the outer layer of the substrate (which can be considered a monomolecular film portion thereof) or monomolecular film applied thereto has a surface which is either receptive to metal plating by electroless techniques or not. Radiation is then used to change the surface to not receptive if it was previously receptive or vice versa, after which a catalyst is used to enhance plating which is then carried out by electroless plating techniques to deposit or not deposit metal in defined areas. When a mask or pattern application is used with irradiation prior to the deposition of the metal, the metal is applied only to a predetermined area and the metal itself can be a mask for later steps. That is the metal layer can be a resist against etching or in the case of printed circuit boards, masks and microwave circuits the metal layer can be the final product. This enables one to fabricate products where the built up metal layer is built up where desired for ultimate use and no metal need be removed.

While specific monolayer films have been described and include specific silanes, other films can be applied to surfaces and can include many different silanes including perflourinated silanes such as tridecafluoro-1,1,2,2-tetrahydrooctyl) -1-dimethylchlorosilane, octadecyldimethylchlorosilane, trifunctional silanes such as trichlorooctenylsilane, trimethoxyoctenylsilane, trimethoxy-4-aminobutylsilane Other materials which are radiation reactive, act as chromophores and which attach to the substrates can be used and include titanates having the general formula $Ti(OR)_4$ where all four of the OR organic groups may be the same or different. These materials and related zirconate and aluminate classes of molecules are recognized to be similar to silanes in that they spontaneously react with surface hydroxyl groups to give an organic monolayer covalently linked to the substrate with the evolution of an alcohol. An O-Ti bond is formed between the surface hydroxyls and the titanates. Titanates such as 2-propanolato-tris (phosphato-O-dioctyl)titanium(IV), UTF12; methoxydiglycolylato-tris-O-(2-propenoato) -titanium(IV), (UTF39); 2-propanolato-tris (3,6-diazahexanolato)titanium(IV), (UTF44) can be used to achieve a selective metal pattern. Other film forming materials for the monolayer can be used which include Langmuir Blodgett films, thiol or disulfide films that assemble on gold surfaces, carboxyls or acid chlorides.

Film thickness of the metal layers deposited can be as known in the electroless plating art for electrical purposes and can be for example 20 nm thick in continuous films with resolution as desired as for example in the 0.5 micron metal width to 0.5 micron spacing width range or lower as for example 0.2 micron metal width to 0.2 micron spacing between metal lines when high energy short wavelength radiation such as 200 nm radiation is used.

In addition to the substrates described above, substrates that can be directly patterned without the use of an additional monomolecular film but which have an outer film carrying a chromophore can be used These substrates can be organic or inorganic materials that have a top surface with a chromophore in the wavelength of interest. Such substrate materials include the following wherein the image to be of metal deposited after irradiation can be negative or positive, that is, a positive image has catalyst adhesion and subsequent metal deposition only in the unirradiated areas of the substrate, whereas a negative image has catalyst adhesion and subsequent metal deposition only in the irradiated areas:

Polyethylene - negative
Paraffin negative
Polypropylene - positive
Polyethylene terephthalate (Mylar) - positive
Polyether polyurethane - positive
Polyisoprene (natural rubber) - positive
Polysulfone - positive
Polymethylmethacrylate (Plexiglas) - positive
Polyacrylic acid - positive
Poly(cis-1,4-butadiene) - negative
Polyurethane - positive
RTV Silicone rubber - positive
Polyethersulfone - positive Obvious modifications that do not depart from the essentials of the invention are apparent to those skilled in semiconductor fabrication or in printed circuitry or in the chemistry of thin films. In view of the changes in the invention that are obvious to such skilled persons, it is intended that the invention not be limited to the precise procedures here described and not to the specific materials used in those procedures. Rather, it is intended that the scope of the invention be construed in accordance with the accompanying claims, having due consideration for changes that merely involve obvious equivalents and for the substitution of materials having known similar properties.

We claim:

1. A process for producing conductive paths on a substrate of the kind having polar functional groups at its surface, comprising the steps of;
    (a) causing a self-assembling monomolecular film to be chemically adsorbed on the surface of the substrate,
    (b) altering the reactivity in regions of the film to produce a predetermined pattern in the film,
    (c) causing a catalytic precursor to adhere only to those regions of the film that have sufficient reactivity to bind the catalytic precursor, and
    (d) placing the substrate in an electroless metal plating bath whereby a metal plate is produced in those regions having the catalytic precursor thereon.

2. The process according to claim 1 wherein the substrate is a semiconductor substance and wherein the self-assembling monomolecular film is a silane of the $R_nSiX_m$ type where;
    R is an organic functional group;
    n = 1,2 or 3;
    m = 4-n; and
    X is selected from the class consisting of a halogen, alkoxy or amine.

3. The process according to claim 1, wherein the substrate is a solid of semiconductive silicon and wherein the self-assembling monomolecular film is produced on the solid by adsorption from a solution containing a chlorosilane.

4. The process according to claim 3, wherein the chlorosilane in solution is 7-octenyldimethylchlorosilane.

5. The process according to claim 3, wherein the chlorosilane in solution is 5-hexenyldimethylchlorosilane.

6. The process according to claim 2, wherein the catalytic precursor is a colloid containing palladium and tin.

7. The process according to claim 6, wherein the substrate is treated sequentially with chemical compounds of tin and palladium to produce a catalytic precursor thereon.

8. The process according to claim 1, wherein the reactivity in regions of the film is altered by irradiating those regions with irradiation that promotes photolytic cleavage of the irradiated regions.

9. The process according to claim 8, wherein the wafer is situated in a vacuum or an inert atmosphere during the irradiation procedure.

10. The process according to claim 9, wherein the irradiation is UV light whose wavelength is less than 200 nm.

11. The process according to claim 10, wherein the self-assembling film is a silane layer.

12. The process according to claim 1, wherein the substrate is a solid of semiconductive silicon having hydroxyl groups on its surface and wherein the self-assembling monomolecular film is bound to the substrate by siloxane bridges to those hydroxyl groups.

13. A process for producing metal paths on a substrate comprising,
selecting a monomolecular film forming the surface of said substrate,
altering the reactivity in regions of said film by irradiating to produce a predetermined pattern in the film,
causing a catalytic reaction to occur only at those regions of the film that have sufficient reactivity to a predetermined catalyst and
placing the substrate in an electroless metal plating bath whereby a metal plate is produced in those regions which have been catalyzed.

14. The process according to claim 13 wherein the substrate is dielectric silicon oxide and the film is produced on the substrate by absorption from a solution containing a chlorosilane.

15. A process according to claim 1 wherein the substrate is alumina and the film is produced from a chlorosilane.

16. A process according to claim 1 wherein the substrate is a conducting metal and the film is produced by absorption from a chlorosilane.

17. A process in accordance with the process of claim 15 wherein the chlorosilane is UTF1.

18. A process in accordance of the process of claim 1 wherein said substrate is selected from the class consisting of semiconductive silicon, dielectric silicon oxide, alumina, metal and quartz and said film is absorbed from a solution containing a silane.

19. A process in accordance with claim 18 wherein the silane is 4-aminobutyldimethylmethoxysilane.

20. A process in accordance with the process of claim 1 wherein the substrate is selected from the group consisting of semiconductive silicon, dielectric silicon, alumina, metal and quartz,
said monomolecular film is absorbed from a solution consisting of a silane or a titanate, said catalytic precursor is a colloid containing palladium and tin, and said metal plate is selected from the group consisting of metals that can be deposited by electroless plating copper, gold, cobalt, nickel, permalloy (iron-nickel-boron alloy) and palladium,
and further comprising placing the substrate in a reactive ion etch to transfer patterns to the substrate followed by stripping the metal with an oxidizing acid.

21. A product produced by the process of claim 1.

22. An electrical device having high resolution metal plate lines produced by the process of claim 13.

23. A process of producing patterned molecular assemblies on a substrate comprising,
providing a substrate having at least one layer of radiation reactive material having substantially equal reactivity over a surface,
exposing said one layer of radiation reactive material to patterned radiation to create spatially separated first and second areas of different reactivity,
building at least one additional layer of material directly on one of said first and second areas to create a patterned on the substrate.

24. A process in accordance with the process of claim 23 wherein said additional layer is selected from inorganic materials, organic materials, semiconductive materials, metals or combinations thereof.

25. A process in accordance with the process of claim 23 wherein said at least one additional layer is a metal.

26. A process in accordance with claim 23 wherein said at least one additional layer comprises two different metal layers.

27. A process in accordance with claim 23 wherein the substrate is a semiconductor substance and wherein the layer of radiation reactive material is a silane of the $R_nSiX_m$ type where:
R is an organic functional group;
n = 1, 2 or 3;
m = 4−n; and
X is selected from the class consisting of a halogen, alkoxy or amine.

28. A process in accordance with claim 27 wherein said at least one additional layer comprises a conductive metal.

29. A process in accordance with claim 28 wherein said silane is a chlorosilane.

30. A process in accordance with claim 23 wherein said building step comprises an electroless plating step.

31. A process in accordance with claim 30 wherein said first mentioned at least one layer is a radiation reactive material and said substrate comprises a second material underlying said reactive material layer.

32. A process in accordance with claim 31 wherein said at least one additional layer comprises a conductive metal.

33. A product produced by the process of claim 23.

34. An electrical device having high resolution metal plate lines produced by the process of claim 32.

* * * * *